US010383968B2

(12) United States Patent
Hobson

(10) Patent No.: US 10,383,968 B2
(45) Date of Patent: Aug. 20, 2019

(54) BATHROOM AIR PURIFICATION AND ODOR REDUCTION SYSTEM

(71) Applicant: David Truong Jonathan Hobson, Langley (CA)

(72) Inventor: David Truong Jonathan Hobson, Langley (CA)

(*) Notice: Subject to any disclaimer, the term of this patent is extended or adjusted under 35 U.S.C. 154(b) by 515 days.

(21) Appl. No.: 14/983,403

(22) Filed: Dec. 29, 2015

(65) Prior Publication Data

US 2017/0183854 A1 Jun. 29, 2017

(51) Int. Cl.
| | |
|---|---|
| *A61L 9/12* | (2006.01) |
| *B01D 46/00* | (2006.01) |
| *B01D 46/44* | (2006.01) |
| *B01D 46/46* | (2006.01) |

(52) U.S. Cl.
CPC .......... *A61L 9/122* (2013.01); *B01D 46/0038* (2013.01); *B01D 46/0045* (2013.01); *B01D 46/44* (2013.01); *B01D 46/46* (2013.01); *A61L 2209/111* (2013.01); *A61L 2209/133* (2013.01); *A61L 2209/14* (2013.01)

(58) Field of Classification Search
CPC .............. A61L 9/122; A61L 2209/111; A61L 2209/133; A61L 2209/14; B01D 46/0038; B01D 46/44; B01D 46/46; B01D 46/0045
See application file for complete search history.

(56) References Cited

U.S. PATENT DOCUMENTS

| | | | |
|---|---|---|---|
| 3,763,505 A | 10/1973 | Zimmerman | |
| 5,369,813 A | 12/1994 | Goddard et al. | |
| 5,488,741 A | 2/1996 | Hunnicutt, Jr. | |
| 5,727,262 A | 3/1998 | Littlejohn | |
| 6,018,824 A | 2/2000 | Pearson | |
| 8,337,602 B2* | 12/2012 | Foerster | A61L 9/014 55/385.1 |
| 9,737,842 B2* | 8/2017 | Matlin | B01D 46/448 |
| 2008/0307570 A1 | 12/2008 | Marks | |
| 2009/0056007 A1 | 3/2009 | Pham | |
| 2010/0089243 A1* | 4/2010 | Bailey | B01D 46/0013 96/222 |

* cited by examiner

*Primary Examiner* — Robert Clemente
(74) *Attorney, Agent, or Firm* — Richard D. Okimaw

(57) ABSTRACT

A bathroom air filtration and odor conditioning device, comprising: a) a square or rectangular housing comprising a bottom portion and four vertical sides; b) a housing lid comprising a plurality of ventilation ports capable of covering a top portion of the housing; c) a filter assembly removably mountable within the housing lid or the housing; d) a plurality of air intake apertures located on a perimeter of the bottom portion of the housing; e) one or more motorized fans capable of creating a partial vacuum that draws the air into through the air intake apertures and exhausts the air through the filter assembly with the air exiting the ventilation ports; f) a power unit; g) one or more sensors; h) one or more scented cartridges; and i) a circuit board unit electrically interconnected to the one or more motorized fans, power unit, one or more sensors and scented cartridges.

15 Claims, 5 Drawing Sheets

BATHROOM AIR PURIFICATION AND ODOR REDUCTION SYSTEM

FIELD OF THE INVENTION

The present disclosure is in the field of bathroom air purification and odor reduction systems.

BACKGROUND OF THE DISCLOSURE

Foul odors in public and private bathrooms are often a nuisance and generally go without a system in place designed to reduce odors and purify the air. Generally, devices available today are not designed to efficiently do both of these tasks to improve air quality. Therefore, there is a need for an efficient automated air filtration and odor conditioning system designed to reduce odors and purify the air.

SUMMARY OF THE INVENTION

A bathroom air filtration and odor reducing device, comprising: a) a square or rectangular housing comprising a bottom portion and four vertical sides; b) a housing lid comprising a plurality of ventilation ports capable of covering a top portion of the housing; c) a filter assembly removably mountable within the housing lid or the housing; d) a plurality of air intake apertures located on a perimeter of the bottom portion of the housing; e) one or more motorized fans capable of creating a partial vacuum that draws the air into through the air intake apertures and exhausts the air through the filter assembly with the air exiting the ventilation ports; f) a power unit; g) one or more sensors; h) one or more scented cartridges removably located between the filter assembly and the housing lid; and i) a circuit board unit affixed within the housing and electrically interconnected to the one or more motorized fans, power unit, one or more sensors and scented cartridges.

DETAILED DESCRIPTION OF THE EMBODIMENTS

The following is a detailed description of certain specific embodiments of the bathroom air filtration and odor conditioning devices disclosed herein. In this description reference is made to the drawings.

Definitions

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

INTRODUCTION

In one aspect, disclosed herein is a bathroom air filtration and odor reducing device, comprising: a) a square or rectangular housing comprising a bottom portion and four vertical sides; b) a housing lid comprising a plurality of ventilation ports capable of covering a top portion of the housing; c) a filter assembly removably mountable within the housing lid or the housing; d) a plurality of air intake apertures located on a perimeter of the bottom portion of the housing; e) one or more motorized fans capable of creating a partial vacuum that draws the air into through the air intake apertures and exhausts the air through the filter assembly with the air exiting the ventilation ports; f) a power unit; g) one or more sensors; h) one or more scented cartridges removably located between the filter assembly and the housing lid; and i) a circuit board unit affixed within the housing and electrically interconnected to the one or more motorized fans, power unit, one or more sensors and scented cartridges, wherein the device automatically activates and provides filtration, purification and elimination and/or reduction of noxious bathroom toilet odors.

Figure 1:
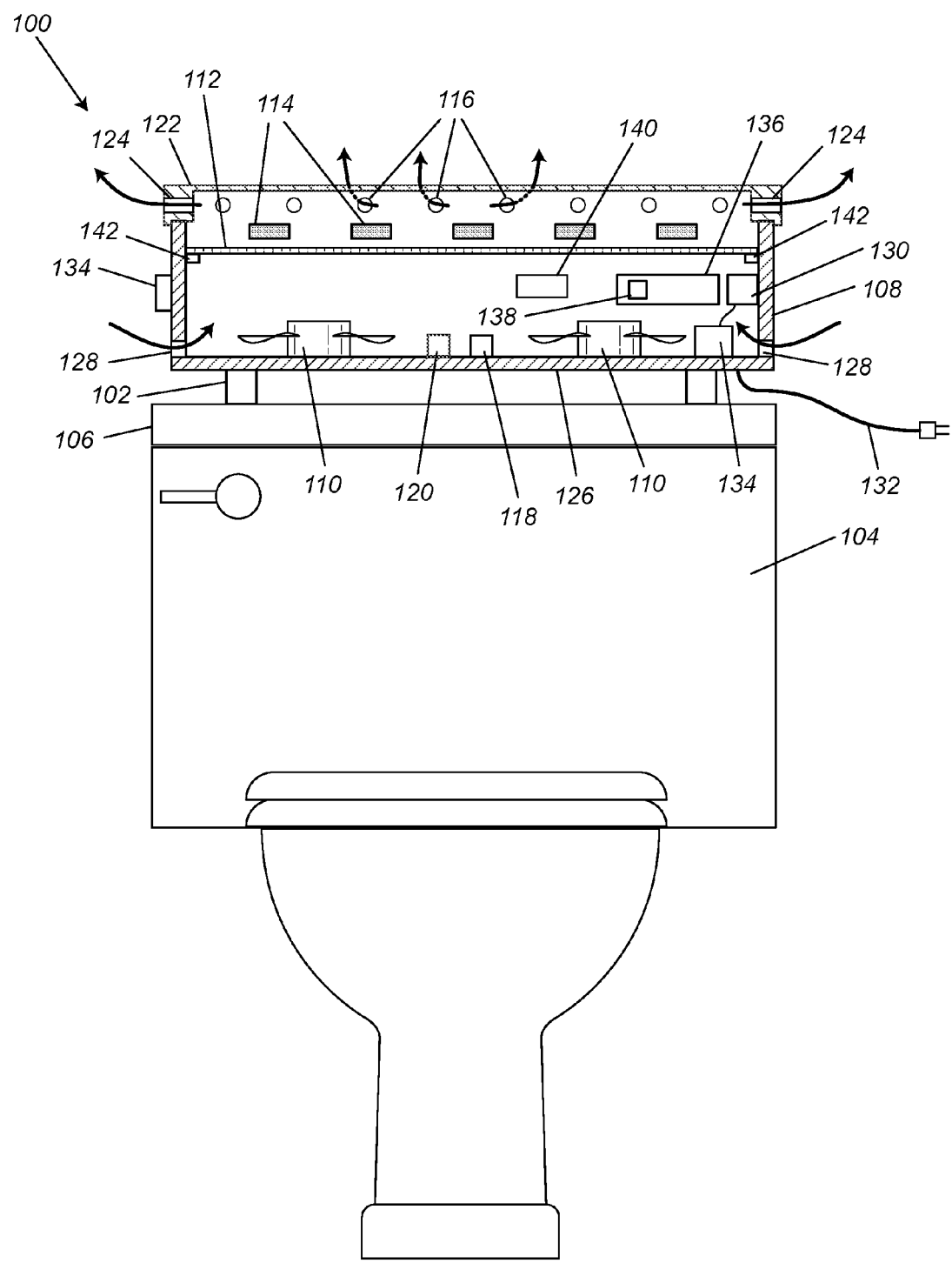
FIG. 1 is a front view illustration of a bathroom air filtration and odor reducing device 100 comprising a housing with a bottom portion 126 and vertical sides 108 mounted on a toilet 104 atop a toilet tank lid 106.

Referring to the drawings, FIG. 1 illustrates a bathroom air filtration and odor reducing device 100, comprising a housing with a bottom portion 126 and vertical sides 108 mounted on a toilet 104 atop a toilet tank lid 106. The housing is constructed of a water resistant material such as a hard plastic. Moreover, the square or rectangular housing comprises one or more motorized fans 110, a circuit board 136, a processor or CPU 138, battery power unit 130, 120V AC power unit 134 and wall outlet power cord 132, a timed duration unit 140, motion sensor 120, battery sensor 118, power ON/OFF switch 134, which are in electronic communication via wires 144. In some embodiments, the bathroom air filtration and odor reducing device further comprises that the power unit comprises a battery power unit and/or a 120V power unit. In some embodiments, the power unit comprises a transformer coupled to receive power from a wall outlet. In some embodiments, the one or more motorized fans is adaptable to selectively receive power from a battery power unit or a wall outlet. Furthermore, the bathroom air filtration and odor reducing device 100 comprises at least one pair of feet 102 affixed to the bottom of the housing whereby the housing is sized to fit atop a toilet tank without being wider or longer than the toilet tank lid. In some embodiments, the device is capable of sitting atop a toilet tank lid via housing feet. In some embodiments, the housing feet provide a gap between the bottom of the housing and the toilet of between about 0.5 inches to about 4 inches. In some embodiments, the bathroom air filtration and odor reducing device 100 has a length of between about 8 inches to about 18 inches, a width of between about 6 inches and about 10 inches and a height of between about 2 inches and about 12 inches. In some embodiments, the bathroom air filtration and odor reducing device 100 has a length of about 16 inches, a width of about 8 inches and a height of about 4 inches. The bathroom air filtration and odor reducing device 100 employs a filter assembly 112 removably mountable within the housing lid 122 or the housing. In some embodiments, the filter assembly 112 is held in place by filter assembly supports 142.

The scented cartridges 114 are in electronic communication with the circuit board 136, battery power unit 130 and/or 120V AC power unit 134, timed duration unit 140, motion sensor 120 and the power ON/OFF switch 134. In some embodiments, the circuit board unit comprises a CPU unit. In some embodiments, the circuit board unit comprises a CPU unit with a manually operable program settings button electrically interconnected to the CPU unit for setting an operational run time for the one or more motorized fans and/or an operational run time for the one or more scented cartridges. In some embodiments, the bathroom air filtration and odor reducing device further comprises a timed duration unit coupled to the one or more motorized fans and the one or more scented cartridges, and controllable to activate the one or more motorized fans and/or the one or more scented cartridges for a period of time. In some embodiments, the bathroom air filtration and odor reducing device further comprises a timed duration unit that is activated by a motion sensor whereby the timed duration unit is in electronic communication with the one or more motorized fans and the one or more scented cartridges, and controllable to activate the one or more motorized fans and/or the one or more scented cartridges for a period of time. In some embodiments, the bathroom air filtration and odor reducing device further comprises a timed duration unit that is activated by a motion sensor whereby the timed duration unit comprises a switch that activates the power unit to operate the one or more motorized fans and/or the one or more scented cartridges, based on movement of a person's body in proximity to the object. In some embodiments, the bathroom air filtration and odor reducing device further comprises a manual switch that can be manipulated by a user to activate the timed duration unit to operate the one or more motorized fans and/or the one or more scented cartridges. The scented cartridges 114 may be any element suitable for deodorizing or masking foul air such as, but not limited to a perfumed material. The scented cartridges 114 may include a combination of elements to deodorize, mask, and/or disinfect the air stream. During the operation of the device the bathroom air is drawn into the housing via the plurality of air intake apertures 128 created by the vacuum from the one or more motorized fans inside the housing, whereby the air is forced through the filter assembly 112 at which time the scented cartridges 114 expel a portion of their contents before the filter and purified air is forced out through the side ventilation ports 124 and top ventilation ports 116. In one embodiment, the housing lid 122 may be opened to change filter assembly 112 or batteries of the battery power unit 130. In some embodiments, the bathroom air filtration and odor reducing device further comprises that the filter assembly is positioned with respect to the casing so as to receive and filter air via air drawn through the air intake apertures and the one or more scented cartridges are positioned between the filter assembly and the ventilation ports of the housing lid for treating the air from the inlet port so as to be fragrant upon passing through the filter and prior to the air exiting via the ventilation ports. In some embodiments, the timed duration unit 140 is activated by a motion sensor and is capable of being adjusted to operate the device for a duration of time between 10 seconds to about 1 minute.

Figure 2:
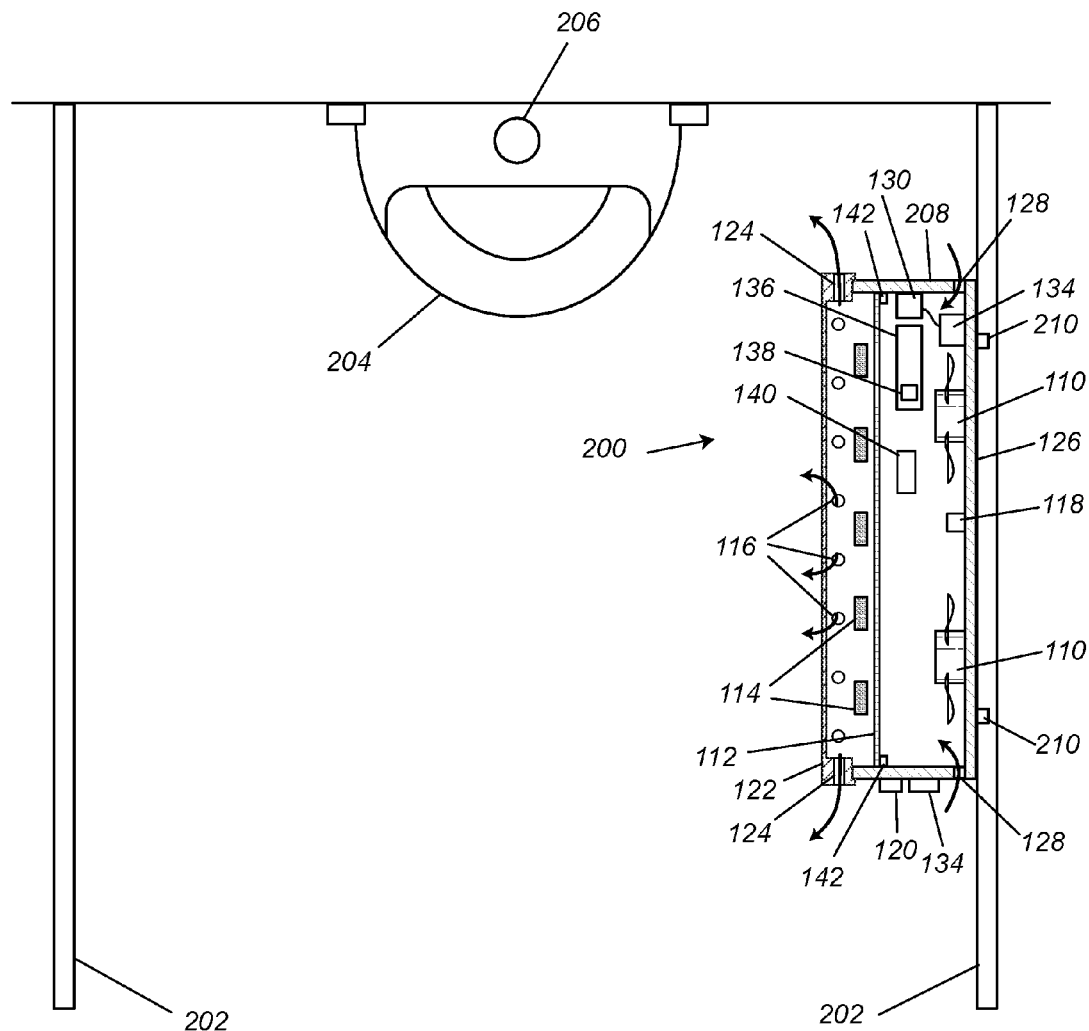
FIG. 2 is a top view illustration of a bathroom air filtration and odor reducing device 200 comprising a fasteners 210, wherein the device is mounted to a bathroom urinal dividing wall 202 adjacent to a wall mounted urinal 204 comprising a wall mounted plumbing pipe 206.
Figure 3:
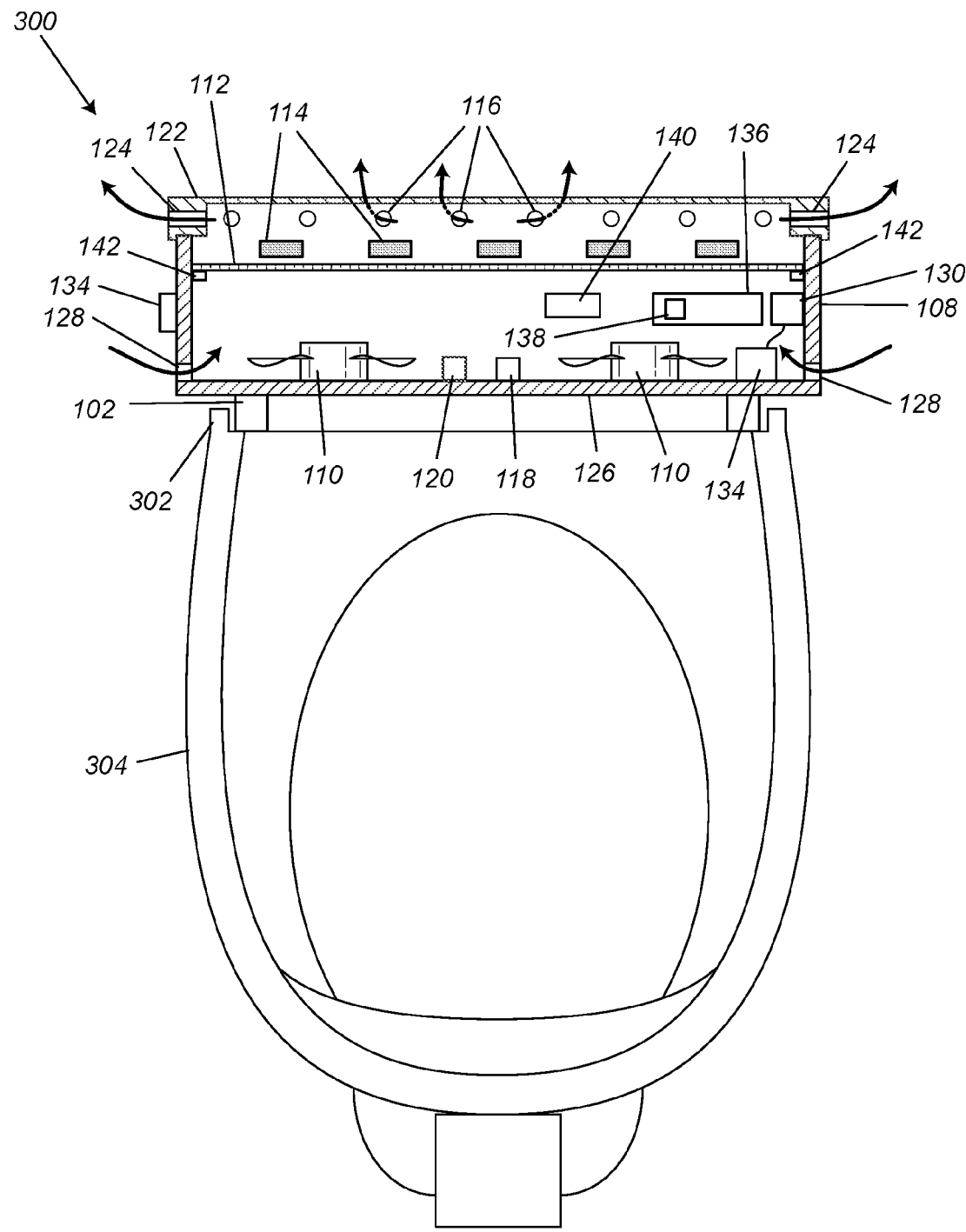
FIG. 3 is a front view illustration of a bathroom air filtration and odor reducing device 300 comprising a housing with a bottom portion 126 and vertical sides 108 mounted atop a urinal 304.

Referring to the drawings, FIG. 2 is an illustration of a bathroom air filtration and odor reducing device 200 is mounted to a bathroom urinal dividing wall 202 adjacent with a plurality of fasteners 210 to a wall mounted urinal 204 comprising a wall mounted plumbing pipe 206. In some embodiments, the bathroom air filtration and odor reducing device 200 is capable of being mounted to a bathroom urinal dividing wall, wherein power is provided by the battery power unit. In some embodiments, the bathroom air filtration and odor reducing device 200 has a length of between about 6 inches to about 18 inches, a width of between about 6 inches and about 12 inches and a height of between about 2 inches and about 6 inches. FIG. 3 is an illustration of a bathroom air filtration and odor reducing device 300 comprising a housing with a bottom portion 126 and vertical sides 108 mounted atop a urinal 304. The bathroom air filtration and odor reducing device 300 is also sized to reside between urinal edges 302 and supported with feet 102. In some embodiments, the bathroom air filtration and odor reducing device 300 is capable of being mounted atop a urinal 304, wherein power is provided by a battery power unit. In some embodiments, the bathroom air filtration and odor reducing device 300 has a length of between about 8 inches to about 18 inches, a width of between about 6 inches and about 10 inches and a height of between about 2 inches and about 12 inches.

Figure 4A:
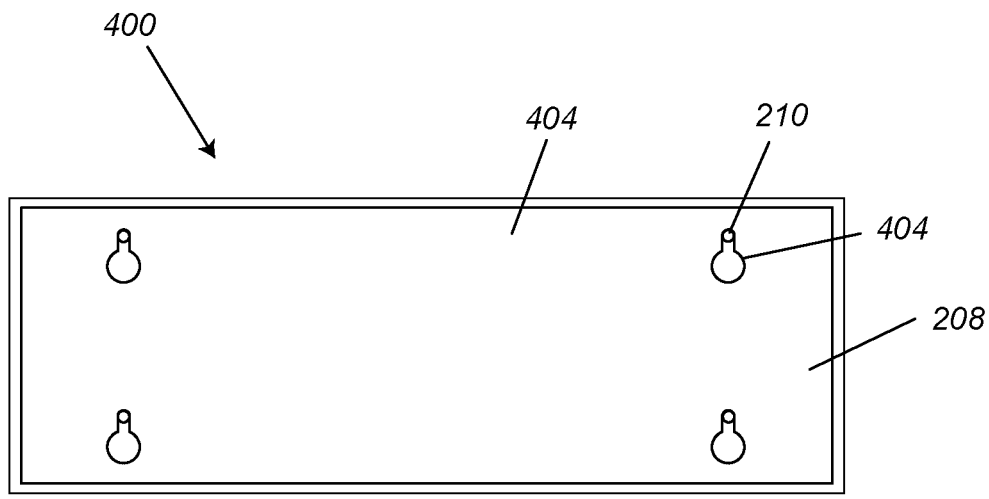
FIG. 4A is an illustration of a view of an outside view of the bottom portion 126 of a bathroom air filtration and odor reducing device 200 comprising vertical sides 208 and a plurality of mount holes 404 used to mount the device to a wall with fasteners 210.
Figure 4B:
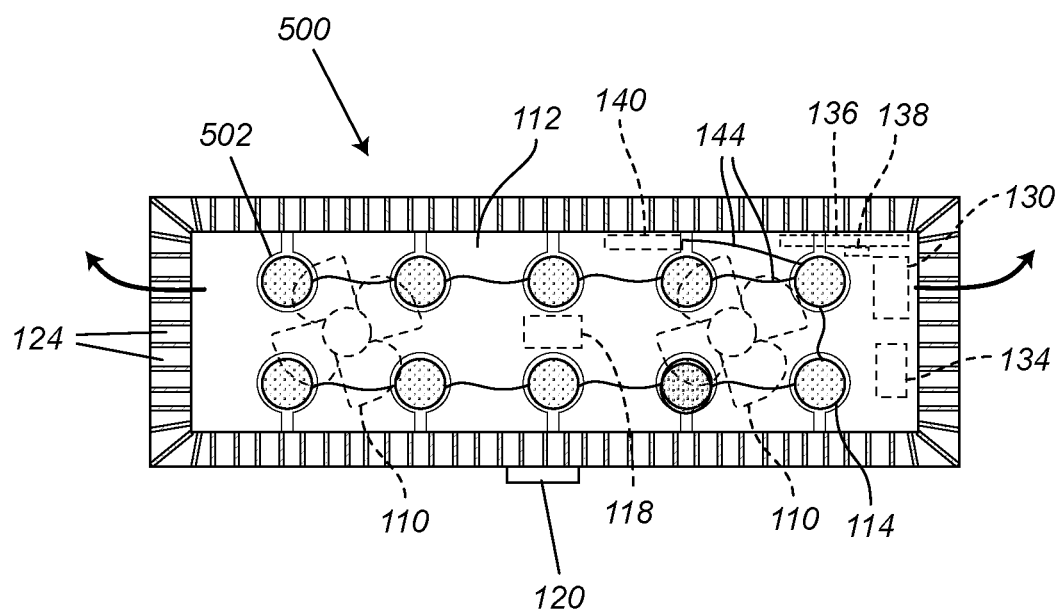
FIG. 4B is a top view illustration of a bathroom air filtration and odor reducing device 500 comprising sensors 120 and 118, a plurality of fans 110, side ventilation ports 124 and scented cartridges 114.

Referring to the drawings, FIG. 4A is an illustration of a view of an outside view of the bottom portion 126 of a bathroom air filtration and odor reducing device 200 comprising vertical sides 208 and a plurality of mount holes 404 used to mount the device to a wall with fasteners 210. In some embodiments, the device is capable of being mounted atop a bathroom urinal, wherein power is provided by a battery power unit. FIG. 4B is a top view illustration of a bathroom air filtration and odor reducing device 500 comprising one or more motorized fans 110, a circuit board 136, a processor or CPU 138, battery power unit 130, 120V AC power unit 134 and wall outlet power cord 132, a timed duration unit 140, motion sensor 120, battery sensor 118, power ON/OFF switch 134, which are in electronic communication. In some embodiments, the bathroom air filtration and odor reducing device 500 is capable of mounted atop a waste disposal can. In some embodiments, the housing feet provide a gap between the bottom of the housing and the waste disposal can of between about 0.5 inches to about 4 inches. In some embodiments, the bathroom air filtration and odor reducing device 500 has a length of between about 6 inches to about 12 inches, a width of between about 6 inches and about 12 inches and a height of between about 2 inches and about 6 inches.

Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be adapted to perform functions and/or features that may be associated with various software elements described throughout.

Figure 5:
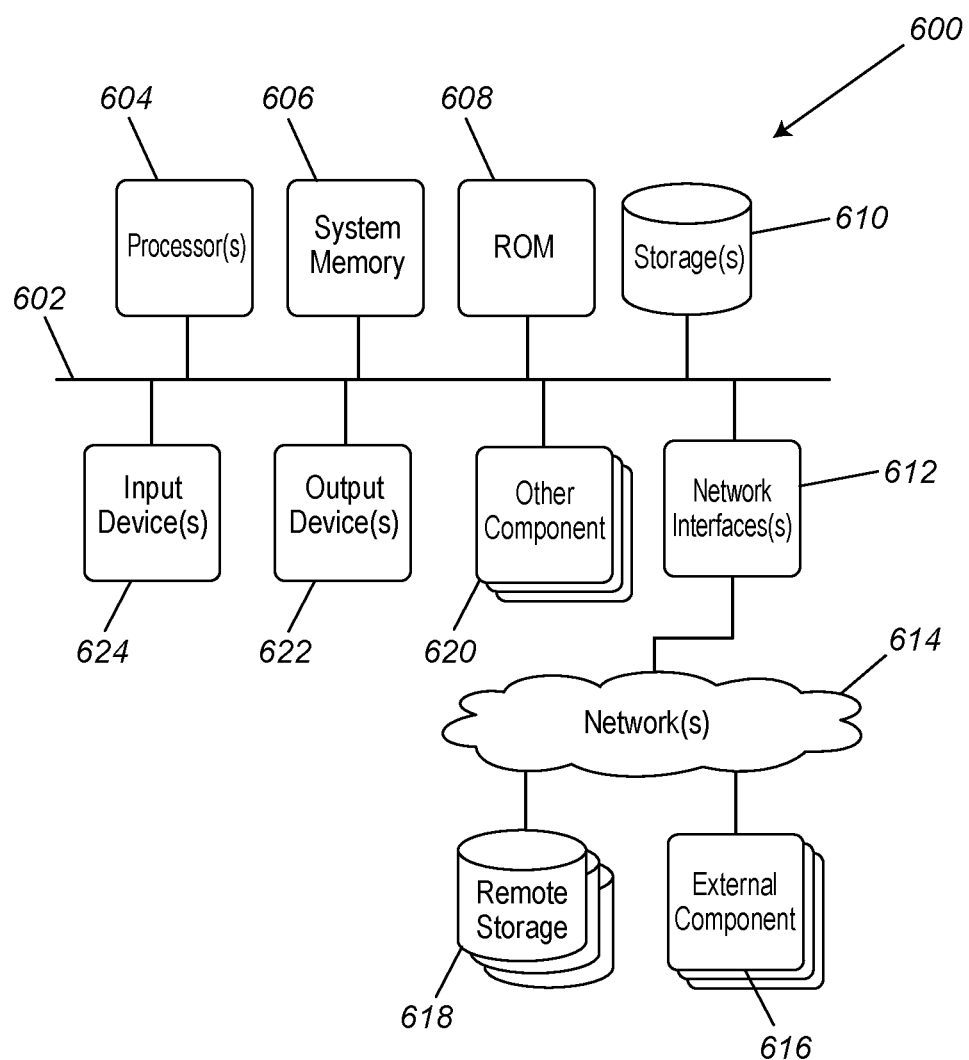
FIG. 5 illustrates a schematic block diagram of a conceptual computer system 600 used to implement some embodiments. For example, the system described above in reference to FIGS. 1, 2, 3, 4A and 4B may be at least partially implemented using computer system 600.

Referring to the drawings, FIG. 5 illustrates a schematic block diagram of a conceptual computer system 600 used to implement some embodiments. For example, the system described above in reference to FIGS. 1, 2, 3, 4A and 4B may be at least partially implemented using all or a portion of computer system 600.

Computer system 600 may be implemented using various appropriate devices. For instance, the computer system may be implemented using one or more vehicle display units, personal computers (PCs), servers, mobile devices (e.g., a smartphone), tablet devices, and/or any other appropriate devices. The various devices may work alone (e.g., the computer system may be implemented as a vehicle display unit) or in conjunction (e.g., some components of the computer system may be provided by a vehicle display unit while other components may be provided by a tablet device).

As shown, computer system 600 may include at least one communication bus 602, one or more processors 604, a system memory 606, a read-only memory (ROM) 608, permanent storage devices 610, input devices 624, output devices 622, various other components 620 (e.g., a graphics processing unit), and one or more network interfaces 612 and may include a network 614, corresponding remote storage 618 and a corresponding external component 616.

Bus represents all communication pathways among the elements of computer system 600. Such pathways may include wired, wireless, optical, and/or other appropriate communication pathways. For example, input devices 624 and/or output devices 622 may be coupled to the system 600 using a wireless connection protocol or system.

The processor 604 may, in order to execute the processes of some embodiments, retrieve instructions to execute and/or data to process from components such as system memory 606, ROM 608, and permanent storage device 610. Such instructions and data may be passed over bus 602.

System memory 606 may be a volatile read-and-write memory, such as a random access memory (RAM). The system memory may store some of the instructions and data that the processor uses at runtime. The sets of instructions and/or data used to implement some embodiments may be stored in the system memory 606, the permanent storage device 610, and/or the read-only memory 608. ROM 608 may store static data and instructions that may be used by processor 604 and/or other elements of the computer system.

Permanent storage device 610 may be a read-and-write memory device. The permanent storage device may be a non-volatile memory unit that stores instructions and data even when computer system 600 is off or unpowered. Computer system 300 may use a removable storage device and/or a remote storage device as the permanent storage device.

Input devices 624 may enable a user to communicate information to the computer system and/or manipulate various operations of the system. The input devices may include keyboards, cursor control devices, audio input devices and/or video input devices. Output devices 622 may include printers, displays, and/or audio devices. Some or all of the input and/or output devices may be wirelessly or optically connected to the computer system.

Other components 620 may perform various other functions. These functions may include performing specific functions (e.g., graphics processing, sound processing, etc.), providing storage, interfacing with external systems or components, etc.

Referring to FIG. 5, computer system 600 may be coupled to one or more networks 614 through one or more network interfaces 612. For example, computer system 600 may be coupled to a web server on the Internet such that a web browser executing on computer system 600 may interact with the web server as a user interacts with an interface that operates in the web browser. Computer system 600 may be able to access one or more remote storages 618 and one or more external components 616 through the network interface 612 and network 614. The network interface(s) 612 may include one or more application programming interfaces (APIs) that may allow the computer system 600 to access remote systems and/or storages and also may allow remote systems and/or storages to access computer system 600 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 600 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The presently disclosed bathroom air filtration and odor conditioning devices are not to be limited in scope by the specific embodiments described herein, which are intended as single illustrations of individual aspects of the presently disclosed devices and methods, and functionally equivalent devices, methods and components are within the scope of the presently disclosed bathroom air filtration and odor conditioning devices. Indeed, various modifications of the presently disclosed bathroom air filtration and odor conditioning devices, in addition to those shown and described herein will become apparent to those skilled in the art from the foregoing description and accompanying drawings. Such modifications are intended to fall within the scope of the appended claims.

What is claimed is:

1. A bathroom air filtration and odor conditioning device, comprising:
   a) a square or rectangular housing comprising a bottom portion and four vertical sides extending from a bottom edge to a top edge;
   b) a housing lid having a plurality of side ventilation ports extending annularly through a side portion of said housing lid at a position proximate to said top edge of said housing capable of covering a top portion of the housing;
   c) a filter assembly removably mountable within the housing lid or the housing;
   d) a plurality of air intake apertures extending through said vertical sides of said housing at a location proximate to said bottom edge thereof;
   e) one or more motorized fans capable of creating a partial vacuum that draws the air into through the air intake apertures and exhausts the air through the filter assembly with the air exiting the ventilation ports;
   f) a power unit;
   g) one or more sensors;
   h) one or more scented cartridges removably located between the filter assembly and the housing lid; and
   i) a circuit board unit affixed within the housing and electrically interconnected to the one or more motorized fans, power unit, one or more sensors and scented cartridges,
   j) wherein said side ventilation ports exhaust air in a direction substantially parallel to the top portion of the housing and perpendicular to the vertical sides,
   wherein the device automatically activates and provides filtration, purification and elimination and/or reduction of noxious bathroom toilet odors.

2. The bathroom air filtration and odor reducing device of claim 1, wherein the circuit board unit comprises a CPU unit.

3. The bathroom air filtration and odor reducing device of claim 1, wherein the circuit board unit comprises a CPU unit with a manually operable program settings button electrically interconnected to the CPU unit for setting an operational run time for the one or more motorized fans and/or an operational run time for the one or more scented cartridges.

4. The bathroom air filtration and odor reducing device of claim 1, further comprising that the power unit comprising a battery power unit and/or a 120V power unit.

5. The bathroom air filtration and odor reducing device of claim 1, wherein the power unit comprises a transformer coupled to receive power from a wall outlet.

6. The bathroom air filtration and odor reducing device of claim 1, wherein the one or more motorized fans is adaptable to selectively receive power from a battery power unit or a wall outlet.

7. The bathroom air filtration and odor reducing device of claim 1, further comprising a timed duration unit coupled to the one or more motorized fans and the one or more scented cartridges, and controllable to activate the one or more motorized fans and/or the one or more scented cartridges for a period of time.

8. The bathroom air filtration and odor reducing device of claim 1, further comprising a timed duration unit that is activated by a motion sensor whereby the timed duration unit is in electronic communication with the one or more motorized fans and the one or more scented cartridges, and controllable to activate the one or more motorized fans and/or the one or more scented cartridges for a period of time.

9. The bathroom air filtration and odor reducing device of claim 1, further comprising a timed duration unit that is activated by a motion sensor whereby the timed duration unit comprises a switch that activates the power unit to operate the one or more motorized fans and/or the one or more scented cartridges, based on movement of a person's body in proximity to the object.

10. The bathroom air filtration and odor reducing device of claim 1, further comprising a manual switch that can be manipulated by a user to activate the timed duration unit to operate the one or more motorized fans and/or the one or more scented cartridges.

11. The bathroom air filtration and odor reducing device of claim 1, wherein the device is capable of sitting atop a toilet tank lid via housing feet.

12. The bathroom air filtration and odor reducing device of claim 1, wherein the device is capable of being mounted to a bathroom urinal dividing wall, wherein power is provided by a battery power unit.

13. The bathroom air filtration and odor reducing device of claim 1, wherein the device is capable of being mounted atop a bathroom urinal, wherein power is provided by a battery power unit.

14. The bathroom air filtration and odor reducing device of claim 1, wherein the device is capable of mounted atop a waste disposal can.

15. The bathroom air filtration and odor reducing device of claim 1, further comprising that the filter assembly is positioned with respect to the housing so as to receive and filter air via air drawn through the air intake apertures and the one or more scented cartridges are positioned between the filter assembly and the ventilation ports of the housing lid for treating the air from the inlet port so as to be fragrant upon passing through the filter and prior to the air exiting via the ventilation ports.

* * * * *